United States Patent [19]

Drake

[11] Patent Number: 4,472,319

[45] Date of Patent: Sep. 18, 1984

[54] PREPARATION OF UNSATURATED NITRILES USING A SURFACTANT

[75] Inventor: Charles A. Drake, Bartlesville, Okla.

[73] Assignee: Phillips Petroleum Company, Bartlesville, Okla.

[21] Appl. No.: 164,871

[22] Filed: Jul. 1, 1980

[51] Int. Cl.$^3$ ............................................ C07C 120/00
[52] U.S. Cl. .................... 260/465.8 R; 260/464; 260/465 H; 260/465 K; 260/465.9
[58] Field of Search ............. 260/464, 465.8 R, 465.9, 260/465 H, 465 K

[56] References Cited

U.S. PATENT DOCUMENTS

| | | | |
|---|---|---|---|
| 2,280,058 | 4/1942 | Bruson | 260/465 H |
| 2,394,962 | 2/1946 | Bruson | 260/464 |
| 2,641,607 | 6/1953 | Albisetti, Jr. et al. | 260/465.9 X |
| 3,840,583 | 10/1974 | Turk | 260/465.9 X |
| 3,929,860 | 12/1975 | Drake | 260/465.9 |
| 3,985,786 | 10/1976 | Drake | 260/465 K |
| 4,001,294 | 1/1977 | Drake et al. | 260/465.8 R |
| 4,117,001 | 9/1978 | Fozzard | 260/465 H X |
| 4,117,002 | 9/1978 | Drake | 260/464 |
| 4,200,586 | 4/1980 | Drake | 260/465.9 X |

OTHER PUBLICATIONS

Albisetti, et. al.; J.A.C.S., 78, (1956), pp. 2637–2641.

*Primary Examiner*—Joseph Paul Brust

[57] ABSTRACT

The process of producing unsaturated dinitriles by reacting an olefinically unsaturated mononitrile, an olefinic hydrocarbon and a monoadduct of an olefinic hydrocarbon and an olefinically unsaturated mononitrile in the presence of an aqueous diluent and a surfactant.

24 Claims, No Drawings

PREPARATION OF UNSATURATED NITRILES USING A SURFACTANT

This invention relates to the production of unsaturated dinitriles. In a specific aspect the invention relates to a reaction of an olefinically unsaturated nitrile, an olefinic hydrocarbon and a monoadduct of an olefinic hydrocarbon and an olefinically unsaturated nitrile in the presence of water to yield olefinically unsaturated dinitrile products having a greater number of carbon atoms than the unsaturated nitrile reactant.

BACKGROUND OF THE INVENTION

In U.S. Pat. No. 2,641,607 (issued June 9, 1953), Albisetti et al describe the thermal reaction of a 2-alkenenitrile (e.g. acrylonitrile) with a neutral olefinic compound (e.g. isobutylene) in a first stage reaction to produce unsaturated mononitriles having a greater number of carbon atoms (e.g. 5-methyl-5-hexenenitrile). Albisetti et al state that the reaction effluent can be distilled to recover the unsaturated mononitrile product, and that the recovered unsaturated mononitrile product can be thermally reacted with a neutral olefinic compound in a second stage reaction to produce unsaturated dinitriles. The patentees state that the first stage reaction can be conducted in the presence or absence of an inert diluent or solvent. The patent lists hydrocarbons, ethers and esters as suitable inert organic solvents, and then states that the reaction also takes place in the presence of water as a diluent, the water serving as a heat transfer medium.

In J. Am. Chem. Soc. 78, pp 2637–2641 (1956), Albisetti et al describe further work with the thermal reaction of a 2-alkenenitrile with a neutral olefinic compound in a first stage and the subsequent reaction in a second stage of a neutral olefinic compound with the reaction product of the first stage to produce unsaturated dinitriles. The authors state that water can be employed as the reaction medium in the second stage reaction of acrylonitrile with 5-methyl-5-hexenenitrile to produce 5-methylenenonanedinitrile. The authors also state that in the case of polymerizable nitriles, the use of water as the medium prevented formation of tars.

In U.S. Pat. No. 3,840,583 (issued Oct. 8, 1974) Turk et al disclose that the yield of unsaturated dinitriles can be increased by contacting an unsaturated mononitrile, an olefin and a monoadduct reaction product of an unsaturated mononitrile and an olefin, wherein the monoadduct reaction product is present in significant amount during substantially the entire reaction period. The patentees stated that this single stage reaction could be carried out in the presence or absence of a solvent or diluent which is nonreactive with either the reactants or the reaction products. The patentees list various hydrocarbons, various ethers, tetrahydrofuran, dioxane, carbon tetrachloride and methylene chloride as representative commercially available nonreactive solvents that can be employed.

A significant improvement over the known processes has been described in U.S. Pat. No. 3,985,786. This patent describes the discovery that the utilization of an aqueous medium as the diluent in the Turk et al single stage process provides a greater increase in yield of unsaturated dinitriles than would be expected from the summation of the increase in yield of unsaturated dinitriles achieved by the utilization of water as the diluent in both stages of the Albisetti et al process and the increase in yield in unsaturated dinitriles achieved by the utilization of the Turk et al single stage reaction instead of the Albisetti et al two stage process.

THE INVENTION

It is one object of this invention to provide a process for the production of unsaturated dinitriles in which the recovery of the diadduct is increased as compared to the known process.

Another object of this invention is to provide a process for the production of the unsaturated dinitrile wherein the production of heavy byproduct is reduced as compared to the known process.

In accordance with this invention, it has now been found that the production of unsaturated dinitriles in a process described in U.S. Pat. No. 3,985,786 is significantly improved when this process is carried out in the presence of a surfactant or emulsifying agent in addition to the water. More specifically, the invention consists in a process for the preparation of olefinically unsaturated dinitriles by contacting an olefinically unsaturated nitrile, an olefinic hydrocarbon containing an allylic hydrogen and a monoadduct reaction product of an olefinic hydrocarbon and an olefinically unsaturated nitrile in the presence of water and a surfactant or emulsifying agent.

Any $\alpha,\beta$-unsaturated mononitrile can be employed in the practice of this invention provided the mononitrile contains ethylenic unsaturation, contains at least one hydrogen atom attached to a doubly bonded carbon atom, and contains a cyano group attached to a carbon atom adjacent and doubly bonded to a carbon atom which is attached to at least one hydrogen atom. Preferably the mononitrile reactant is free of acetylenic unsaturation and contains from 1 to 2 ethylenically unsaturated, nonconjugated double bonds as the sole aliphatic unsaturation, while the total number of carbon atoms in the mononitrile reactant is within the range of 3 to 18, more preferably within the range of 3 to 8. Illustrative unsaturated mononitrile reactants include those represented by the formula

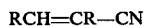

RCH=CR—CN wherein each R is independently selected from the group consisting of hydrogen and hydrocarbyl radicals. Preferably the hydrocarbyl radicals are selected from the group consisting of alkyl, cycloalkyl, and aryl hydrocarbyl radicals and combinations thereof, such as alkylcycloalkyl, cycloalkylalkyl, aralkyl and arylcycloalkyl radicals. Examples of unsaturated nitriles meeting the requirements, of the above formula are acrylonitrile, methacrylonitrile, 2-decenentrile, 3-cyclohexyl-2-propenenitrile, 4-phenyl-2-butenenitrile, 3(p-tolyl)-2-propenenitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-octenenitrile, 2-octadecenenitrile, 6,7,8-trimethyl-9-phenyl-2-nonenenitrile, 5-p-tolyl-2-nonenenitrile, and the like, and mixtures thereof.

Any acyclic of cyclic olefinic hydrocarbon compound can be employed in the practice of this invention, provided that the compound has at least one olefinic linkage having joined to one of the doubly bonded carbons a carbon atom having at least one hydrogen atom attached thereto, said doubly bonded carbon atoms being free of cyano groups attached thereto. The olefinic hydrocarbons preferably are free of acetylenic unsaturation and have from 3 to 18 carbon atoms per molecule with from 1 to 2 ethylenically unsaturated, nonconjugated double bonds as the sole aliphatic unsaturation. The preferred types of these compounds are the open chain monoolefinic hydrocarbons represented by the formula $R'_2C=CR'-CHR'_2$, wherein each $R'$ is independently selected from the group consisting of hydrogen and hydrocarbyl radicals, said hydrocarbyl radicals being selected from the group consisting of alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the ethylenic linkage. Specific examples of olefinically unsaturated hydrocarbon compounds which are useful in the process of this invention include propylene, isobutylene, diisobutylene, triisobutylene, 1,5-hexadiene, beta-pinene, 1,5-cyclooctadiene, 2,4,4-trimethyl-1-pentene, 2-butene, biallyl, bimethallyl, alpha-methylstyrene, beta-methylstyrene, 1-pentene, 1-decene, cyclohexene, 1-allylcyclohexene, 3-allylcyclohexane, 4-allylcyclohexene, allylbenzene, 3,4,4-trimethyl-2-pentene, 1-dodecene, 2,3-dimethyl-2-butene, and 2-methyl-1-phenyl-2-propene, and the like, and mixtures thereof.

Suitable monoadduct reactants include any monoadduct reaction product of an olefinic hydrocarbon, as hereinabove defined, and an unsaturated mononitrile as hereinabove defined. It is believed that the olefinic hydrocarbon compound and the unsaturated mononitrile react in accordance with the "ene" reaction to produce, as the principal monoadduct reaction product, a compound having the structural formula

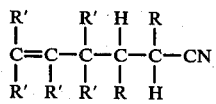

Generally, a lesser amount of an isomeric monoadduct reaction product having the formula

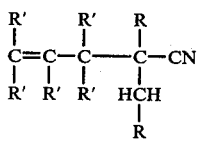

is also produced. Thus, isobutylene and acrylonitrile react to produce 5-methyl-5-hexenenitrile as the principal monoadduct reaction product along with a small amount of 2,4-dimethyl-4-pentenenitrile. It can be readily seen that isobutylene as the olefinic hydrocarbon reactant possesses six of the required allylic hydrogens but that all six are structurally equivalent so that only two monoadduct reaction compounds corresponding to the above general formulas are produced according to the ene reaction.

However, it will also be evident that if a compound having two or more allylic hydrogens which are not structurally equivalent is employed as the olefinic hydrocarbon reactant, the number of expected isomeric monoadduct reaction product compounds having the above general formulas will be increased. For example, if 2,4,4-trimethyl-1-pentene is reacted with acrylonitrile the major monoadduct reaction products expected according to the "ene" reaction would be 5-methylene-7,7-dimethyloctanenitrile and 4-methylene-2,6,6-trimethylheptanenitrile with lesser amounts of 5,7,7-trimethyl-5-octenenitrile and 4,t-butyl-5-methyl-5-hexenenitrile. Other factors not fully understood at present may influence the relative amounts of the possible isomers in the monoadduct reaction product and in other instances presently employed analytical methods may not distinguish the various isomers present. Indeed, the monoadduct reaction product finds utility in many applications with no need of a costly separation of the isomers present in the monoadduct reaction product. The isomer mixture reaction product produced by the reaction of an olefinic hydrocarbon and an olefinically unsaturated nitrile can be employed as the monoadduct reactant, or one or more isomers can be separated from the isomeric mixture reaction product and such separated isomer or isomers can be employed as the monoadduct reactant. Examples of suitable monoadduct reactants include 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentenenitrile, 2-ethyl-4-methyl-4-pentenenitrile, 2(n-butyl)-4-pentenenitrile, 2-(n-butyl)-5-phenyl-4-pentenenitrile, and mixtures thereof.

The diadduct reaction products obtained by the process of this invention comprise the reaction product mixtures formed by the monoaddition of an unsaturated mononitrile and any monoadduct reaction product. Exemplary of a diadduct reaction product is the reaction product mixture consisting of the major isomer species 5-methylenenonanedinitrile and 5-methyl-4-nonenedinitrile, and contains minor isomer species 2-methyl-4-methylene octanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

Any amount of olefinic hydrocarbon, olefinically unsaturated mononitrile and monoadduct reaction product can be employed in the practice of this invention. In general the mol ratio of olefinically unsaturated mononitrile reactant to olefinic hydrocarbon reactant will be in the range of about 10:1 to about 0.1:1, preferably in the range of about 5:1 to about 0.2:1, and more preferably in the range of about 2:1 to about 0.3:1. In general the monoadduct reaction product will be employed in an amount such that during substantially the entire reaction period the net monoadduct reaction product present in the reaction mixture will consitute from about 10 to about 90, preferably from about 20 to about 80, and more preferably from about 30 to about 70 weight percent of the total reaction mixture. The net amount of monoadduct reaction product present in the reaction zone is the sum of the amount of monoadduct reaction product charged to the reaction zone plus the amount of monoadduct reaction product produced by the reaction of the olefinic hydrocarbon reactant and the olefinically unsaturated mononitrile reactant in the reaction zone less the monoadduct reaction product consumed by reaction with the olefinically unsaturated mononitrile in the reaction zone to produce diadduct. The monoadduct reaction product charged to the reaction zone can be the same as or different from the monoadduct reaction product produced by the reaction of the olefinic hydrocarbon reactant and the olefinically unsaturated mononitrile reactant in the reaction zone, but it will be generally preferred for them to be the same. The total reaction mixture includes all fluid materials present in the reaction zone, i.e. reactants, diluents, products, byproducts, etc.

Any suitable reaction conditions for either a batch process or a continuous process can be employed in the practice of the invention. The reaction time employed in the practice of this invention can vary widely. Generally a time period of from about two minutes to about 48 hours, preferably from about 30 minutes to about 10 hours, and more preferably from about 1 hour to about 5 hours is an adequate period of time for olefin, unsaturated mononitrile and a monoadduct reaction product to be suitably admixed in the preparation of reaction products in high yields in a batch process. In a continuous process the liquid hourly space velocity will generally be in the range of about 0.05 to about 20, preferably in the range of about 0.1 to about 10, more preferably in the range of about 0.5 to 2.

The reaction temperatures that can be employed in the practice of the invention can vary widely. Generally, however, suitable reaction temperatures are within the range of from about 100° C. to about 500° C., and preferred reaction temperatures are within the range of from about 200° C. to about 350° C.

The reaction pressures suited to the practice of this invention also vary widely. Reaction pressures within a range of from about atmospheric pressure to about 100,000 psig can be employed; however, reaction pressures within the range of from about 500 psig to about 4000 psig are preferably employed.

If desired, the processes of this invention can be carried out in the presence of a polymerization inhibitor. The use of the inhibitor often advantageously limits side reactions such as the dimerization or polymerization of the olefinically unsaturated mononitrile. When an inhibitor is employed, it is generally desirable that an amount of from about 0.001 to about 5, preferably from about 0.1 to about 1, precent by weight inhibitor based on the weight of unsaturated mononitrile reactant be employed. Suitable inhibitors include hydroquinone, 2,6-di-tert-butyl-para-cresol, 2,6-di-tert-butylhydroquinone, 4-tert-butyl-catechol, para-hydroxydiphenylamine, and the like, and combinations thereof.

The reaction of the above described olefinic hydrocarbon reactant, olefinically unsaturated mononitrile reactant and monoadduct reaction product reactant is carried out in the presence of an aqueous diluent, preferably comprising at least 50 weight percent water, more preferably at least 80 weight percent water, and more preferably consisting essentially of water. The codiluent, if employed, can be any solvent or diluent which is nonreactive with either the reactants or the reaction products. Examples of suitable codiluents include benzene, toluene, para-xylene, ortho-xylene, meta-xylene, ethylbenzene, diethyl ether, ethyl propyl ether, dibutyl ether, tetrahydrofuran, dioxane, cyclohexane, carbon tetrachloride, methylene chloride, and the like, and mixtures thereof.

The diluent can be employed in any suitable amount. In general the diluent will be employed in an amount in the range of about 0.01 to about 40 parts by weight of total diluent per part by weight of olefinically unsaturated mononitrile reactant charged to the reaction zone. The amount of diluent currently preferred is in the range of about 0.1 to about 20 parts by weight of total diluent per part by weight of olefinically unsaturated mononitrile reactant charged to the reaction zone. The advantages of the aqueous diluent system include improved selectivity to the desired olefinically unsaturated nitrile and reduced amounts of heavy polymeric byproduct. This latter byproduct is particularly objectionable because it tends to foul reactor surfaces.

Any of the well-known surfactants (surface active agents) or emulsifiers are useful in the practice of this invention. Thus, anonic, cationic, or nonionic surfactants are suitable for use in the preparation of olefinically unsaturated dinitriles according to the present invention. It is currently preferred to employ anionic or nonionic surfactants. Exemplary of the well-known and often commercially available anionic surfactants are the sodium, potassium, ammonium, and amine salts of carboxylic acids, sulfonic acids, sulfate esters, and phosphate esters, such as sodium stearate, potassium laurate, sodium dodecylbenzenesulfonate, sodium octly sulfate, ammonium salt of sulfate ester of nonylphenoxytri(ethyleneoxy)ethanol and sodium 2-ethylhexylphosphate. Many nonionic surfactants are likewise well-known and commercially available, including glycerol esters of fatty acids and polyethylene glycol esters, such as nonylphenoxypoly(ethyleneoxy)ethanol. Included in the useful cationic surfactants are the well-known quaternary ammonium hydroxides. The useful surfactants generally contain from 8–40 and preferably 12–24 carbon atoms per molecule.

The amount of surfactant employed in the present invention will vary over a wide range depending, of course, on the desired results. Generally, from 0.01 to 10, preferably from 0.1 to 1, percent by weight of surfactant based on weight of $\alpha,\beta$-unsaturated mononitrile will be sufficient to give the desired degree of conversion of reactants to products and the desired selectivity to the desired products.

The following isomerization prevention step does not in itself constitute an embodiment of this invention but only in combination with the use of water and surfactant describes a preferred embodiment of this invention. In order to avoid unwanted double bond isomerization of ingredients such as the above-described monoadduct reaction product, it is frequently desirable to include in the reaction mixture a small amount of an alkali metal salt of a di-, tri-, or tetracarboxylic acid as an isomerization inhibitor. Such salts generally contain from two to about twelve carbon atoms per molecule. Potassium salts are preferred. Exemplary salts include the potassium or other alkali metal salts of oxalic acid, malonic acid, succinic acid, azelaic acid, citric acid, cyclopentane 1,2,3,4-tetracarboxylic acid and the like. The amount of inhibitor can be selected over a rather wide range but will generally be in the range of about 0.0001 to about 10 percent by weight and preferably 0.0005 to 2 weight percent based on the weight of the least stable isomer.

A convenient method of carrying out this invention comprises heating a mixture of an olefinically unsaturated mononitrile (e.g. acrylonitrile), an olefinic hydrocarbon compound (e.g. isobutylene), and a monoadduct reaction product reactant (e.g. a mixture of 5-methyl-5-hexenenitrile and 2,4-dimethyl-4-pentenenitrile, water, surfactant and optionally potassium oxalate) in a reaction pressure vessel at a temperature within the range of about 200° to about 350° C. and at pressures of from about 500 to about 4000 psig, the mol ratio of the olefinically unsaturated mononitrile to the olefinic hydrocarbon being in the range of about 5:1 to about 0.2:1, and the concentration of the monoadduct reaction product reactant in the reaction mixture being in the range of about 20 to about 80 weight percent. Thereafter, the resulting olefinically unsaturated dinitrile reaction product is readily isolated from the reaction effluent mixture by any convenient product recovery method, such as fractional distillation. The reaction can be promoted indefinitely, in apparatus well known in the art and suited to either batch or continuous reaction conditions, until the mononitrile reactant and/or the olefinic hydrocarbon reactant, is depleted from the reaction media.

If desired, the reaction can be carried out in the presence of any suitable promoter, for example an organo derivative of a Group VA element defined by the following formula $R'''_n ZH_{3-n}$ wherein each R''' is independently selected from the group consisting of aryl, alkaryl, cycloalkylaryl, aralkyl, aryloxy, alkaryloxy, arylaryloxy; wherein each R''' group contains from 6 to 12 carbon atoms; Z is selected from the group consisting of $$N, P, \overset{O}{\underset{\|}{P}},$$

As, Sb, or Bi; and n is 2 or 3. Illustrative of organo derivatives of the Group VA elements defined by the above formula are the following compounds: triphenylphosphine, diphenylphosphine, tris(hexylphenyl)phosphine, tris(cyclohexylphenyl)phosphine, dinaphthylphosphine, tris(4-biphenyl)phosphine, tris(4-butylphenyl)phosphine, triphenylamine, diphenylamine, tris(3,5-dipropylphenyl)amine, triphenylarsine, tris(pentylphenyl)arsine, triphenylbismuthine, diphenylarsine, diphenyl-4-biphenylphosphine, tris(p-tolyl)stibine, tris(3,5-dimethylphenyl)bismuthine, diphenyl(4-ethylphenyl)phosphine, diphenoxy(phenyl)phosphine, diphenyl(p-methylphenoxy)phosphine, triphenylphosphite, diphenyl(p-tolyl)phosphine, triphenylphosphate, and the like, and mixtures thereof. The variant designated by n in mixtures of promoters represented by the formula $R'''_n ZH_{3-n}$ can vary, with the arithmetical sum of the value of n of individual promoters, from 2 to 3. The term "reaction promoting material" includes materials commonly called catalysts as well as materials commonly called promoters.

If employed, the amount of promoter utilized in the process of this invention can vary widely. In general, the mol ratio of promoter to unsaturated mononitrile reactant charged to the reaction zone would be in the range of about 1:20 to about 1:1. Preferably, the mol ratio of promoter to unsaturated mononitrile reactant charge would be in the range of about 1:10 to about 1:3.

The following examples are presented in further illustration of the invention but should not be unduly construed in limitation thereof.

EXAMPLE I

The following comparative run 1 illustrates the preparation, according to the prior art, of a mixture of olefinically unsaturated dinitriles (hereinafter called diadduct) from acrylonitrile, isobutylene, and a monoadduct reaction product of acrylonitrile and isobutylene containing predominantly 5-methyl-5-hexenenitrile with a small amount of 2,4-dimethyl-4-penenenitrile.

Through a series of three 300 cc reactors maintained at 280° C. and 17,000 kPa (2500 psig) was pumped a mixture of acrylonitrile (1590 g), isobutylene (2915 g) and monoadduct (7456 g) at a rate of 17.8 mL/min. with an average residence time in the reactors of 0.6 hour. Water containing 0.001 percent by weight potassium oxalate (based on total water and potassium oxalate) was pumped into the reactor train at 0.75 mL/min.

After four hours of feed flow through the reactor train, a sample of reaction product mixture was collected for one hour. The collected product mixture was allowed to stand at room temperature and pressure for the volatiles (predominantly isobutylene) to evaporate. Fractional distillation and analysis of fractions by gas-liquid chromatography gave the results shown in Table I.

EXAMPLE II

The following inventive run 2 illustrates the preparation of diadduct from acrylonitrile, isobutylene and monoadduct in the presence of a nonionic surfactant.

Run 2 was carried out as described in Example I except that 2879 g isobutylene was employed and the added water solution contained 0.53 weight percent Triton ™ X405, nonionic surfactant, an octylphenoxy polyethoxy ethanol commercially available from Rohm and Haas Co., as well as, the above-described 0.001 weight percent potassium oxalate (the weight percent values based on total water, surfactant and potassium oxalate).

The analysis of the resultant product mixture fractions is given in Table I.

EXAMPLE III

The following inventive run 3 illustrates the preparation of diadduct from acrylonitrile, isobutylene, and monoadduct in the presence of sodium stearate, a known anionic surfactant.

Run 3 was carried out as described for Example I except that 2880 g isobutylene was employed and the added water solution contained 0.53 weight percent sodium stearate, as well as, the above-described 0.001 weight percent potassium oxalate (the weight percent values based on total water, sodium stearate, and potassium oxalate).

The analysis of the resultant product mixture fractions is given in Table I.

TABLE I

| Run No. | Surfactant | Conv., %[a] | Yield, %[d] | | | |
|---|---|---|---|---|---|---|
| | | | MA[b] | DA[c] | Dimer | Heavies |
| 1 (prior art) | none | 52.8 | 1.8 | 76.2 | 3.7 | 14.4 |
| 2 (inv.) | nonionic | 58.4 | 0.3 | 84.7 | 3.4 | 12.9 |
| 3 (inv.) | anionic | 55 | 1.4 | 81.9 | 3.1 | 12.3 |

[a]Percent of acrylonitrile converted to products.
[b]Percent increase in monoadduct compared to amount charged to reactor.
[c]Diadduct contains predominantly 5-methyl-1,9-nonanedinitrile and 5-methyl-4-nonenedinitrile with minor amounts of other isomers.
[d]Percent yield of products based on amount of acrylonitrile converted to products The results in Table I show that use of a surfactant in the reaction mixture of Runs 2 and 3 resulted in higher conversion of acrylonitrile to products, higher yield of desired diadduct and lower yield of undesirable heavies than in prior art Run 1.

Reasonable variations and modifications which will become apparent to those skilled in the art can be made in this invention without departing from the spirit and scope thereof.

I claim:

1. In a process comprising reacting olefinically unsaturated mononitrile reactant, olefinic hydrocarbon reactant and monoadduct reactant being the reaction product of olefinic hydrocarbon compound and an olefinically unsaturated mononitrile compound, both said olefinic hydrocarbon reactant and said olefinic hydrocarbon compound having at least one allylic hydrogen, both said olefinically unsaturated mononitrile reactant and olefinically unsaturated mononitrile compound being represented by the formula

RCH=CR—CN wherein each R is independently selected from the group consisting of hydrogen and hydrocarbyl radicals, said reaction taking place in the presence of aqueous diluent to produce unsaturated dinitriles, the improvement comprising carrying out the reaction in the presence of a surfactant.

2. Process in accordance with claim 1 wherein said reaction is carried out under reaction conditions suitable to produce at least one olefinically unsaturated dinitrile product, each of said olefinic hydrocarbon reactant and said olefinic hydrocarbon compound having at least one olefinic linkage having joined to one of the doubly bonded carbons a carbon atom having at least one hydrogen atom attached thereto, wherein during substantially the entire reaction period the concentration of said monoadduct reaction product in the resulting reaction mixture is within the range of about 10 to about 90 weight percent of the total reaction mixture.

3. A process in accordance with claim 2 wherein each of said at least one olefinic hydrocarbon reactant and said olefinic hydrocarbon compound is free of acetylenic unsaturation and has from 3 to 18 carbon atoms per molecule with from 1 to 2 ethylenically unsaturated, nonconjugated double bonds as the sole aliphatic unsaturation.

4. A process in accordance with claim 3 wherein each of said at least one olefinically unsaturated mononitrile reactant and said olefinically unsaturated mononitrile compound is free of acetylenic unsaturation, has from 1 to 2 ethylenically unsaturated, nonconjugated double bonds as the sole aliphatic unsaturation, and has from 3 to 18 carbon atoms per molecule.

5. A process in accordance with claim 4 wherein each of said at least one olefinic hydrocarbon reactant and said olefinic hydrocarbon compound is represented by the formula R'$_2$C=CR'—CHR'$_2$, wherein each R' is independently selected from the group consisting of hydrogen and hydrocarbyl radicals.

6. A process in accordance with claim 5 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

7. A process in accordance with claim 5 wherein said reaction conditions comprise a temperature in the range of about 200° C. to about 350° C., a pressure in the range of about 1000 to about 4000 psig, a contact time in the range of about 30 minutes to about 10 hours, and a mole ratio of said olefinically unsaturated mononitrile reactant to said olefinic hydrocarbon reactant in the range of about 5:1 to about 0.2:1; and wherein said at least one monoadduct reaction product comprises compounds having the structural formula

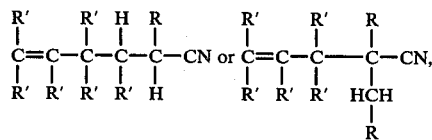

wherein each R' is independently selected from the group consisting of hydrogen and hydrocarbyl radicals and each R is independently selected from the group consisting of hydrogen and hydrocarbyl radicals; and further comprising recovering from the resulting reaction effluent said at least one olefinically unsaturated dinitrile reaction product.

8. A process in accordance with claim 6 wherein said diluent consists essentially of water.

9. A process in accordance with claim 8 wherein during substantially the entire reaction period said concentration of monoadduct reaction product in said reaction mixture is maintained within the range of about 20 to about 80 weight percent.

10. A process in accordance with claim 9 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

11. A process in accordance with claim 1 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

12. A process in accordance with claim 11 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

13. A process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, in the presence of an aqueous diluent, under reaction conditions suitable to produce at least one olefinically unsaturated dinitrile product; wherein each of said at least one olefinic hydrocarbon reactant and said olefinic hydrocarbon compound has from 3 to 18 carbon atoms and is represented by the formula R'$_2$C=CR'—CHR'$_2$, wherein each R' is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula RCH=CR—CN, wherein each R is independently selected from the group consisting of hydrogen and hydrocarbyl radicals;

wherein said at least one monoadduct reaction product comprises compounds having the structural formula $$\begin{array}{c} \text{R'} \quad \text{R'} \quad \text{H} \quad \text{R} \\ | \quad | \quad | \quad | \\ \text{C}=\text{C}-\text{C}-\text{C}-\text{C}-\text{CN} \\ | \quad | \quad | \quad | \\ \text{R'} \quad \text{R'} \quad \text{R'} \quad \text{H} \end{array} \quad \text{or} \quad \begin{array}{c} \text{R'} \quad \text{R'} \quad \text{R} \\ | \quad | \quad | \\ \text{C}=\text{C}-\text{C}-\!\!-\!\!-\text{C}-\text{CN}, \\ | \quad | \quad | \quad | \\ \text{R'} \quad \text{R'} \quad \text{R'} \quad \text{HCH} \\ \phantom{XXXXXXXXXX} | \\ \phantom{XXXXXXXXXX} \text{R} \end{array}$$

wherein R and R' are as defined above;

wherein said at least one olefinically unsaturated dinitrile product is formed by the monoaddition of a said olefinically unsaturated mononitrile reactant and a said monoadduct reaction product;

wherein said aqueous diluent comprises at least 50 weight percent water; the balance, if any, of said diluent being nonreactive with the reactants and the reaction products;

wherein the amount of said aqueous diluent is in the range of about 0.01 to about 40 parts by weight per part by weight of said at least one olefinically unsaturated mononitrile reactant;

wherein said reaction conditions comprise a temperature in the range of about 100° C. to about 500° C., a pressure in the range of about atmospheric to about 100,000 psig, and a reaction time in the range of about two minutes to about 48 hours for a batch process or a liquid hourly space velocity in the range of about 0.05 to about 20 for a continuous process;

wherein the mol ratio of said at least one olefinically unsaturated mononitrile reactant to said at least one olefinic hydrocarbon reactant is in the range of about 10:1 to about 0.1:1; and wherein during substantially the entire reaction period the concentration of said monoadduct reaction product in the resulting reaction mixture is within the range of about 10 to about 90 weight percent of the total reaction mixture;

wherein the reaction is carried out in the presence of a surfactant.

14. A process in accordance with claim 13 wherein said diluent comprises at least 80 weight percent water.

15. A process in accordance with claim 14 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

16. A process in accordance with claim 15 wherein said diluent consists essentially of water.

17. A process in accordance with claim 16 further comprising recovering from the resulting reaction effluent said at least one olefinically unsaturated dinitrile reaction product.

18. A process in accordance with claim 13 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

19. A process in accordance with claim 1 wherein said diluent consists essentially of water.

20. A process in accordance with claim 1 wherein each of said at least one olefinic hydrocarbon reactant and said olefinic hydrocarbon compound has from 3 to 18 carbon atoms and is represented by the formula $R'_2C=CR'—CHR'_2$, wherein each R' is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula $RCH=CR—CN$ wherein each R is independently selected from the group consisting of hydrogen and hydrocarbyl radicals.

21. A process in accordance with claim 20 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1; and wherein said aqueous diluent comprises at least 50 weight percent water; the balance; if any, of said diluent being monoreactive with the reactants and the reaction products; the amount of said diluent being in the range of about 0.01 to about 40 parts by weight per part by weight of said at least one olefinically unsaturated mononitrile reactant.

22. A process in accordance with claim 1 wherein said surfactant is selected from the group consisting of nonionic surfactants, anionic surfactants, and mixtures thereof.

23. A process in accordance with claim 1 comprising carrying out the reaction in the presence of an isomerization inhibitor.

24. A process in accordance with claim 23 wherein said isomerization inhibitor is an alkali metal salt of a polycarboxylic acid containing 2 to 4 carboxylic groups per molecule.

* * * * *